United States Patent [19]

Boughton

[11] 4,182,314

[45] Jan. 8, 1980

[54] MULTI-CHANNEL VASCULAR FLOW MONITORING SYSTEM

[76] Inventor: Morris W. Boughton, 3332 Donna Dr., Carlsbad, Calif. 92008

[21] Appl. No.: 814,315

[22] Filed: Jul. 11, 1977

[51] Int. Cl.² .............................. A61B 5/02; A61B 5/05
[52] U.S. Cl. ...................................... 128/693; 128/734
[58] Field of Search ...................... 128/2.05 V, 2.05 F, 128/2.1 Z; 73/194 E; 324/65 R, 64; 364/416

[56] References Cited

U.S. PATENT DOCUMENTS

| | | | |
|---|---|---|---|
| 3,131,689 | 5/1964 | Rodler | 128/2.1 Z |
| 3,678,296 | 7/1972 | Day | 128/2.1 Z X |
| 3,742,936 | 7/1973 | Blanie et al. | 128/2.1 Z |
| 3,802,419 | 4/1974 | Yates | 128/2.1 Z X |
| 3,835,839 | 9/1974 | Brown | 128/2.05 F |
| 3,871,359 | 3/1975 | Pacela | 128/2.1 Z |
| 3,874,368 | 4/1975 | Asrican | 128/2.1 Z |
| 3,882,851 | 5/1975 | Sigworth | 128/2.1 Z |
| 3,971,365 | 7/1976 | Smith | 128/2.1 Z |
| 3,994,284 | 11/1976 | Voelker | 128/2.05 F |

Primary Examiner—Lee S. Cohen
Attorney, Agent, or Firm—Knox & Knox

[57] ABSTRACT

A multi-channel vascular flow monitoring system for measuring skin resistance during peripheral blood flow. Conventional EKG type electrodes supply current flow through a selected segment of skin and monitor voltage across a plurality of selected areas within the current supplied segment. Separate detectors are utilized for amplifying and filtering voltage signals received from the voltage electrodes. The detectors provide a first output voltage representing percentage of resistance changes across the voltage electrodes and a second output signal representing the resistance of each monitored skin segment. The output signals of all of the detectors are normalized by a common reference voltage and either directly displayed or further conditioned for use with various display medium.

11 Claims, 5 Drawing Figures

MULTI-CHANNEL VASCULAR FLOW MONITORING SYSTEM

BACKGROUND OF THE INVENTION

The invention relates generally to impedance plethysmography and more specifically to electronic means for monitoring changes in a plurality of separate skin segments of a human responsive to peripheral blood flow adjacent thereto.

Prior art methods of monitoring skin segments response to blood flow include multiple frequency impedance systems that require balancing of each impedance bridge frequencies manually prior to the taking of measurements. This system had restricted use due to the fact that they were very sensitive and required a laboratory environment for reasonable operation. Also, the maximum number of channels available are limited due to potential harmonic distortions between the impedance systems.

Other state of the art impedance measurement systems provided for self balancing frequency bridge circuits providing for use in other than laboratory environments, however, these systems are limited to single channel operation.

These and other means impedance measuring systems fail to provide for simultaneous monitoring of a plurality of separate skin areas within a skin segment.

This and other monitoring limitations have not been resolved until the emergence of the instant invention.

SUMMARY OF THE INVENTION

The present invention obtains the various benefits from the prior vascular flow monitoring art and improves their operational efficiency by providing the benefit of simultaneous monitoring of a plurality of skin areas within a given skin segment.

In accordance with the invention, there is provided an improved multi-channel plethysmograph system.

The plethysmograph system of the instant invention is characterized by a multi-channel system that provides for a wide range of dynamic input while maintaining a constant loop bandwidth over the entire dynamic range. A unique high Q band pass filter is provided for canceling substantially all of the undesirable noise caused by external cabling, external pick up electrodes, and the 1/F amplifier noise. Gain controls for each channel provide for their normalization. An acquisition aid is provided to aid the feedback loop in decreasing the time for equipment stability.

The main object of this invention is to provide an accurate, noise free, multi-channel plethysmography system.

Another object of this invention is to provide a decrease in the span of time between initial attachment of the pick up electrodes and a useable system output signal.

Still another object of this invention is to maintain loop stability over a large dynamic range of input voltage signals.

The above and other features of the present invention will be readily apparent as the description continues while being read in conjunction with the appended drawings.

DESCRIPTION OF THE PREFERRED EMBODIMENT

Figure 1:
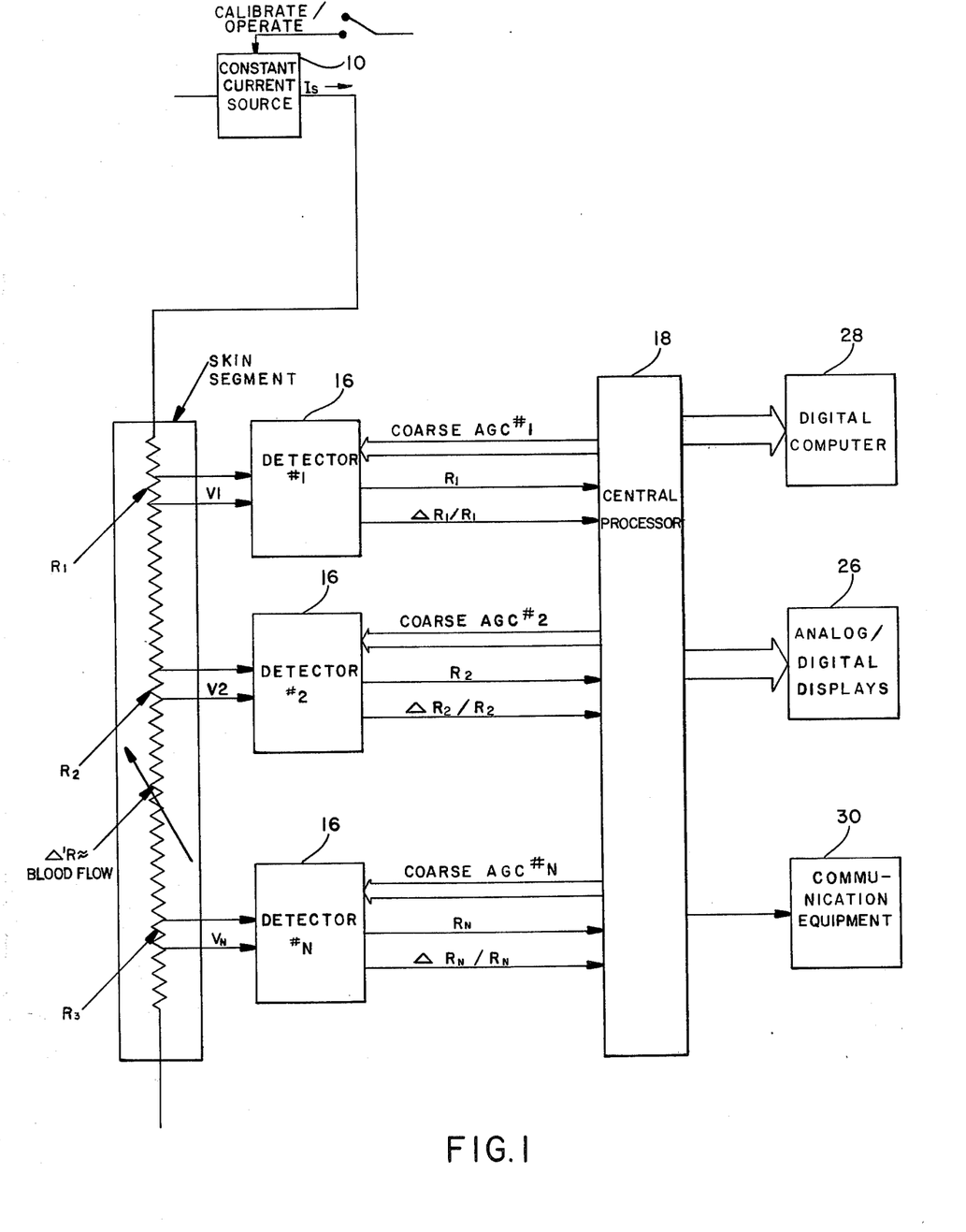
FIG. 1 shows a block diagram of the system.

FIG. 1 shows a block diagram of a multiple channel vascular flow monitoring system of the present invention. A constant current source 10 generates an AC current $I_s$ (typically 50 KHZ) which is applied to a given biological segment (typically skin). A plurality of voltage pick up means (typically EKG type electrodes) are positioned in line with the skin segment and supply a voltage input to an associated detector means 16. Any number of small skin segments may be monitored within the current applied skin area. Each detector 16, see FIG. 2, comprises an input amplifier 17 with automatic gain control (fine AGC) to provide the correct gain for normalization of the peak to peak AC voltage monitored at an associated skin segment. The output of the AC amplifier 17 is applied to an AC/DC converter 19 whose output becomes a DC representation of the peak to peak signal from the output of amplifier 17. The input AC voltage $V_N$ to each detector 16 is also converted to a DC voltage through a second AC/DC converter 21. This DC voltage from the second converter 21 is representative of the actual resistance Rn of that monitored skin area. The now DC output voltage from the first AC/DC converter 19 is summed at summing network 23 with a reference voltage Vref (which is common to all of the summing networks utilized in the system). This summed voltage is further amplified by DC amplifier 25. The output of DC amplifier 25 is fed back as AGC to AC amplifier 17. The detector 16 is considered balanced when the DC component of the AGC signal is 0 volts. The AC component of the signal (typically 0.5 $H_z$ to 5 $H_z$) represents percentage change in resistance Rn. This $\Delta$Rn/Rn signal is the true representation of blood flow within the associated skin segments.

Figure 2:
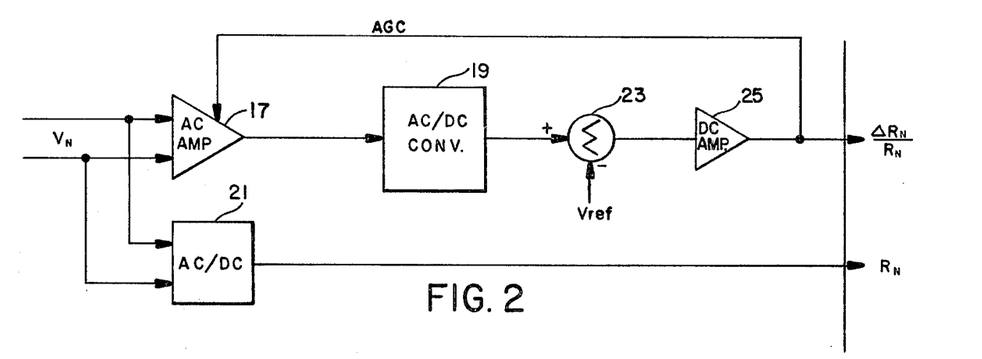
FIG. 2 shows a block schematic of a typical detector.

It is well known that as blood flows in the vicinity of a skin segment, the skin segment resistance changes proportionally. Therefore, the AC voltage $V_N$ developed across the skin segment due to the constant current Is provides an amplitude modulation which represents the percentage change in blood flow within that given sample of the skin segment. The information bandwidth of this phenomenon is typically in the range of from 0.5 Hz to approximately 5 Hz. This requires that the bandwidth of converter 19 be approximately 0.2 Hz to 7 Hz (−3 db range). This allows the AC components of the output voltage from amplifier 25 (whose DC component provides the fine AGC feedback voltage) to represent the percentage change in skin resistance due to blood flow as $\Delta$Rn/Rn.

Referring now to FIG. 1, these $\Delta$Rn/Rn voltage signals are fed into a central processor 18. One of the functions of the central processor 18 is to sense the magnitude of the resistance sample Rn and provide digital processing to feedback a course AGC voltage signal to aid the detector 16 in providing the amplification necessary to achieve balance. Another purpose of this central processor 18 is to multiplex, digitize and process the $\Delta$Rn/Rn and the Rn signals from each detector. The central processor additionally provides the digitized outputs for further processing by digital computers 28 and analog/digital displays 26. The central processor may further provide PCM telemetry outputs 30 for transmission to remote locations.

Figure 3:
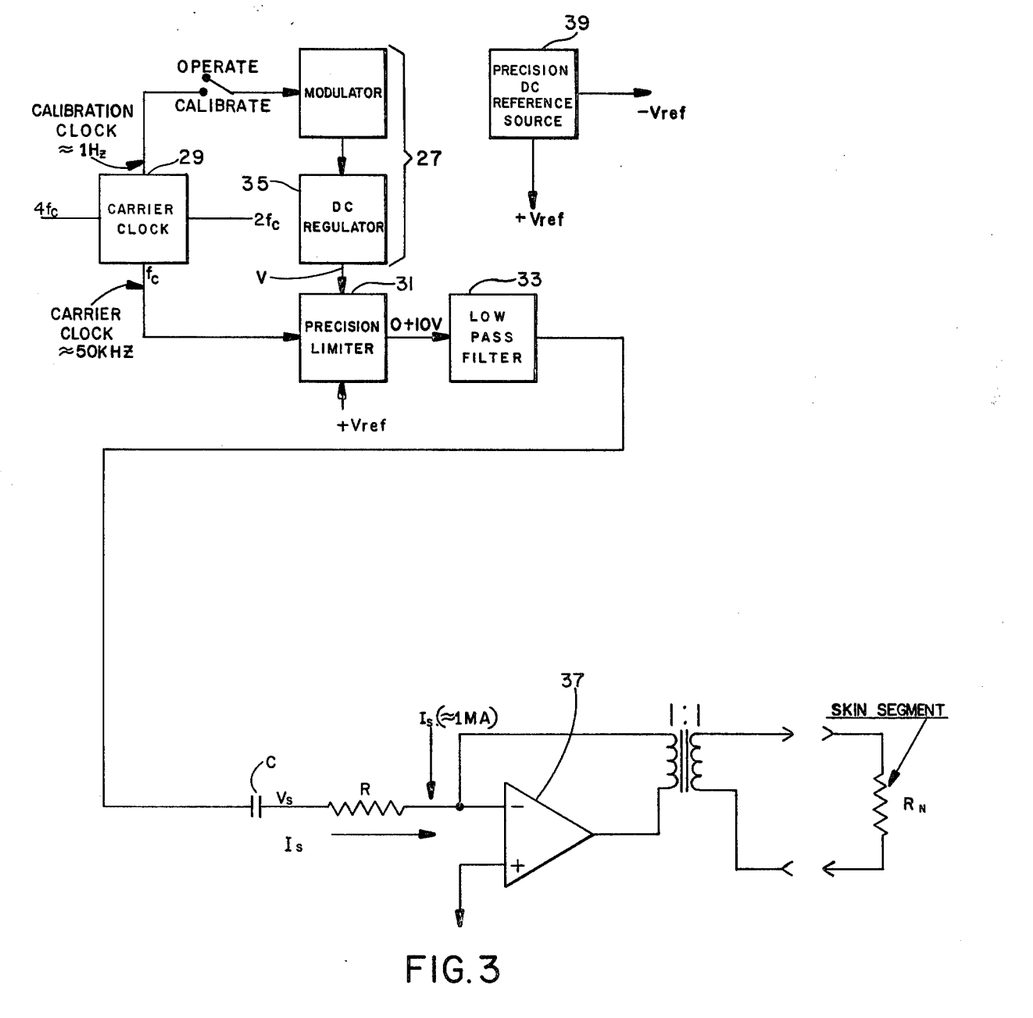
FIG. 3 shows a block diagram of the calibration and constant current source utilized in the invention.

FIG. 3 is a block diagram showing of a precision constant current source 10 and a DC calibration reference source 27. The current source 10 and reference source 27 are derived from well known design techniques. A carrier clock 29 (approximately 50 KH$_z$) provides a 50 KH$_z$ input signal to a precision limiter 31 which provides a precision output peak to peak voltage to a low-pass filter 33. The amplitude of this peak to peak voltage from the limiter 31 is determined by reference voltage V from a DC regulator 35. Low pass filter 33 is designed to remove all of the add harmonics from the applied precision peak to peak carrier clock square wave signal. The output of the low pass filter 33 provides the voltage source Vs which is applied through a capacitor C and fixed resistor R to the summing junction of a high quality wideband operational amplifier 37. As is well known in operational amplifier technology, the current Is resulting from the application of Vs across resistor R to the summing junction to the amplifier (which is effectively 0 volts) must be matched by an equal current fed back around the amplifier 37 through the 1:1 transformer primary back to the summing junction. Therefore, when the chosen skin segment is applied across the secondary of the 1:1 transformer, the precise current Is, typically set to 1 ma. RMS, is applied through the skin segment, independent of the skin segment resistors Rn.

The pecision DC reference source 39 provides the precision DC reference source voltage $-V_{ref}$ to all detectors 16 utilized in the system for providing input AC voltage normalization.

Figure 4:
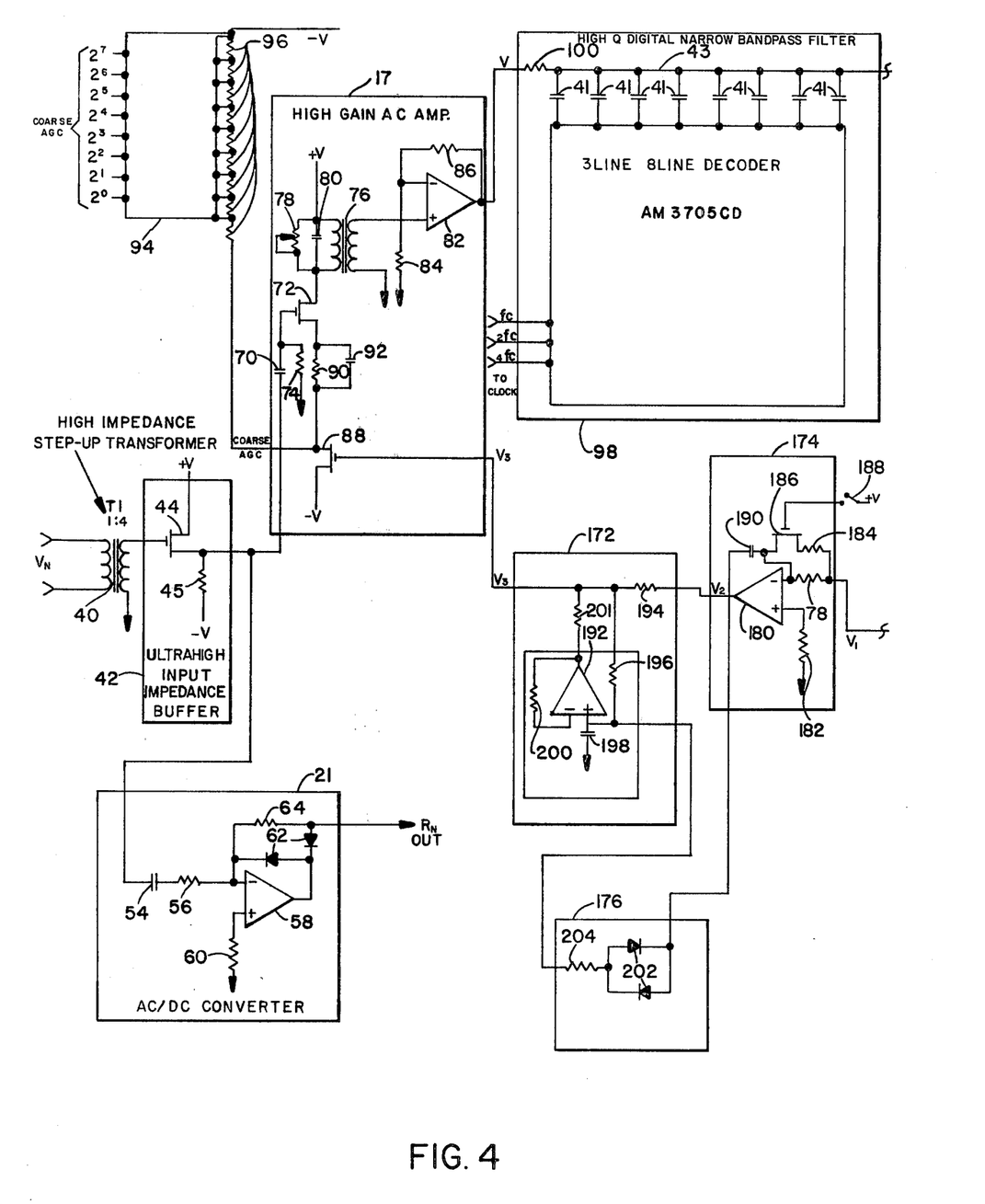
FIG. 4 shows a detailed schematic of a portion of the detector.
Figure 5:
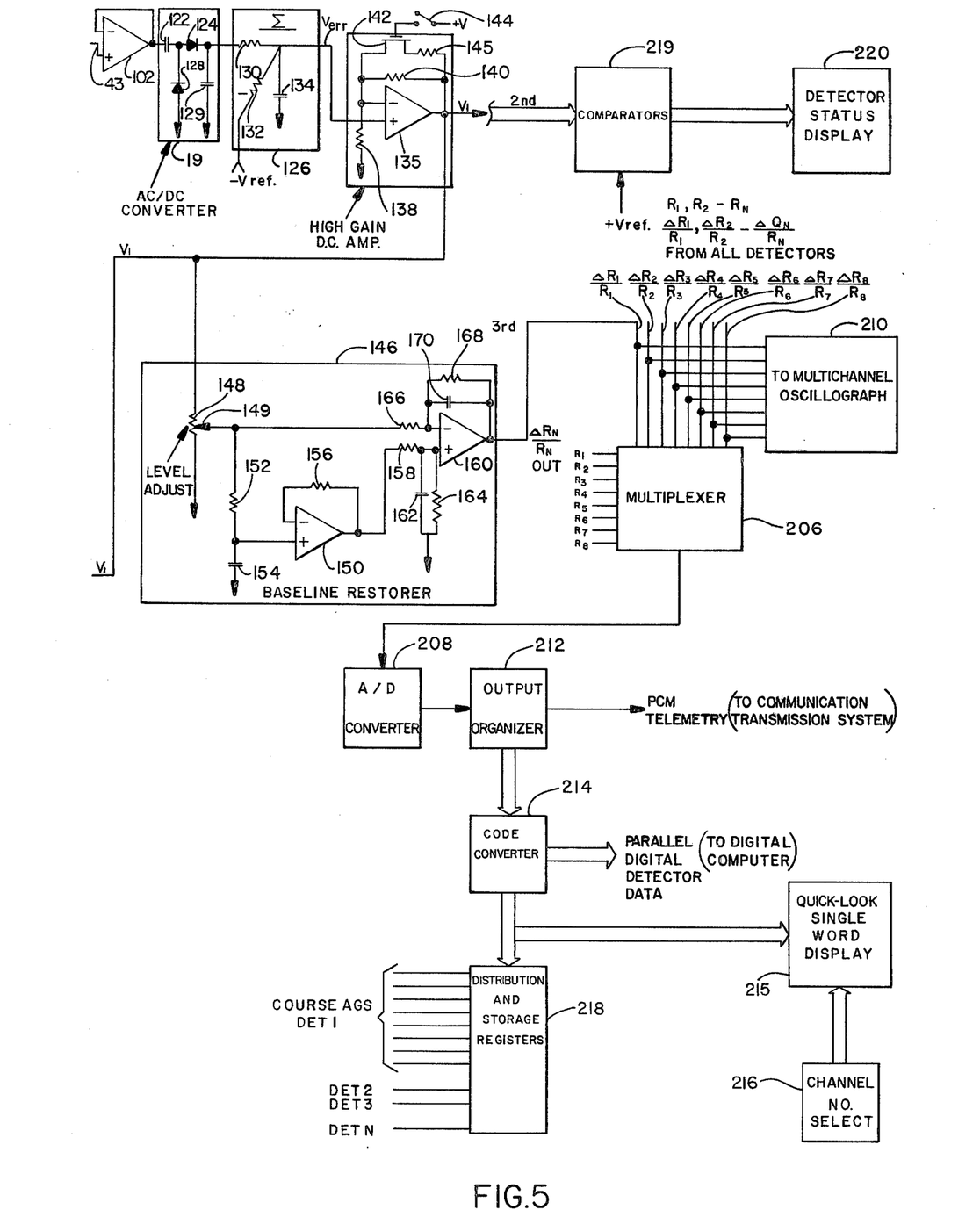
FIG. 5 shows a detailed schematic of a portion of the detector, not shown in FIG. 4 and typical signal condition and display blocks.

Referring now to FIGS. 4 and 5, these figures are a detailed showing of a portion of one of the pluralities of detectors used in the device. All of the detectors are exactly alike electronically so for ease of explanation, only one will be described. The detector is comprised of three major elements: the front end, discriminator, and loop filter.

The front end consists of an extremely high quality, high impedance, step up transformer 40 having a ratio of 1:4. This transformer 40 presents to the resistance between the voltage pick up means an impedance at 50 KHz of greater than 20 K ohms. The output secondary of transformer 40 is applied to an extremely high input impedance buffer stage 42 which exhibits an impedance of greater than 2 megohms at 50 KHz. The buffer stage 42 consists of a MOS FET transistor 44 with its gate element connected to one end of the secondary of transformer 40, the other end of the transformer secondary tied to the system common potential. The drain element transistor 44 is connected to the source of the positive operating potential. A MOS FET transistor of the type M122 or equivalent is chosen because of its high frequency electrical properties and minimum drain due to gate element capacitance, thus allows for its input impedance to be greater than 2 megohms at 50 KHz. The buffer stage 42 is of a source follower configuration with the source element of the transistor applied to both the high gain AC amplifier 17 and the AC/DC converter 21.

The AC/DC converter 21 comprises a conventional operational rectifier. The source element of transistor 44 is connected to the source of the negative operating potential through resistor 45 of 2 K ohms and through a series capacitor 54 of a 0.1μ capacitor and a resistor 56 of 20 K ohms of the 1% MF type to the negative input to operational amplifier 58 of the type CA3140 whose positive input is connected through resistor 60 of 10 K ohms to negative system common potential. The negative input to the operational amplifier 58 is connected to its output through two parallel paths. One path includes a series diode 62 and the other path comprises a series resistor 64 of 20 K ohms of the 1% MF type and a second diode 62 both diodes are of the type 1N4454.

The high-gain amplifier 17 is of a unique design which provides an input voltage dynamic range from 40 milli-volts (MV) to 8 volts (V) RMS. The output from the buffer 42 is connected through a capacitor 70 of 1000 pf to the gate element of transistor 72. A resistor 74 of 10 K ohms is connected to the junction between capacitor 70 and the gate element of transistor 72 and the system ground potential. The drain element of transistor 72 is connected to one end of the tuneable primary of a transformer 76. the opposite end of the tuneable primary winding of transformer 76 is connected to the positive potential. Connected in parallel to the secondary of tuneable transformer 76 is a variable resistor 78 having a range of from 100 K ohms to 1 megohm and a capacitor 80 of 1000 pf. The secondary of the transformer 76 is connected at one end to the system ground potential and at its other end to the positive input element of operational amplifier 82 of the type CA3140. The negative input to operational amplifier 82 is tied through resistor 84 of 100 K ohms to the system ground potential. A resistor 86 of a range of from 50 K-150 K ohms, the exact value determined as hereinafter explained is connected from the amplifier negative input to the amplifier output. The source element of transistor 72 is connected to the drain element of transistor 88 of the type M116 through the series parallel combination of resistor 90 of 1.5 K ohms and capacitor 92 of 0.1 μf. The gate element of transistor 88 is connected to the fine AGC control voltage $v_3$ hereinafter discussed. The source element of transistor 88 is connected to the negative system potential $-V$. The drain element of transistor 88 is also connected to the coarse AGC voltage supplied from digital resistance converter 94, hereinafter described. Transistor 72 is a high frequency MOS FET whose gain is determined by the ratio of the effective drain impedance presented by transformer 76 and resistor 78 to the effective source resistance provided by the resistance generated by the digital/resistance converter 94. The resistance of transistor 88 is determined by the fine AGC control voltage $V_3$. Resistor 90 determines the maximum drain current allowable on transistor 72. Parallel capacitor 92 (of 0.1 μf) provides extremely low AC impedance across resistor 90 at 50 K Hz, therefore, the value of resistor 90 has no effect on the effective source resistance of transistor 72. Transformer 76 is a high impedance 1:1 transformer. The characteristics of this transformer are chosen to allow for greater than 10 milli-amps (MA) of DC current to pass through the primary, without saturation, and in addition, allow provision for tuning to a center frequency of 50 K Hz. Resistor 78 provides a pad across the primary of transformer 76 to normalize the maximum gain at this point at a constant value for each of the detectors. The secondary of transformer 76 is applied through operational amplifier 82 which has relatively low gain (typically less than 2), with the exact value of gain determined by resistors 86 and 84.

The digital/resistance coverter 94 consists of a pair of DG200 MOS FET switches, each having two inputs and four outputs. The inputs being connected to the digital signal from the central processor 18 which provides course AGC signal as hereinafter described. The pairs of outputs from each driven gate are connected across a resistor of a series binary weighted resistor network 96. The least significant switch (2°) controls the lowest resistor value (2 K ohms) and so on, with the most significant switch controlling the highest resistor value (512 K ohms). Each adjacent one of said pairs are interconnected with one end of the series connected to the negative system potential −V and the opposite end tied to the hereinbefore mentioned drain element of transistor 88. The coarse AGC digital input to the MOS FET switches comes from the central processor 18 or may come from a single analog to digital converter having a memory. This signal is an eight-bit binary weighted representation of the measured initial source resistance Rn stored in a memory device. Depending upon the binary value of the coarse AGC, any one of the resistors of network 96 may be shorted out of the circuit by lack of an input signal, thus providing an incremental binary-weighted set of resistances which, when properly selected, provided the optimum resistance across the transistor 88 to maintain a relatively coarse AGC feedback voltage independent of the source resistance Rn. This digital/resistance converter allows the system to have a constant loop bandwidth over the entire dynamic range of Rn.

Referring now specifically to FIG. 4, the output voltage from the high-gain AC amplifier 17 is applied to the input of a high Q digital narrow bandpass filter 98 having a bandpass of 7 Hz. The characteristics of this filter are unique, in that it has a Q of 7000 and yet provides perfect center frequency stability maintained at the exact center frequency of the input Ac voltage independent of environmental effects. This filter provides substantially 80 db of noise rejection of all noise components outside of the fundamental frequency of 50 K Hz. The narrow bandpass filter 98 includes a 3 line-8 line decoder of the AM3705Cd type. Each of the outputs from the internal switching network of the line decoder has a 0.1 µf capacitor 41. These capacitors are tied together at one end by a common conductor 43. The input end of the common conductor 43 is connected to the output of the high-gain amplifier 17 through resistor 100 of 36 K ohms. The output end of the common conductor 43 is connected to the positive input of operational amplifier 102. Amplifier 102 has its negative input connected to its output to provide unity gain. The three frequency inputs f, 2f and 4f to the 3 inputs of the high Q digital narrow bandpass filter 98 are provided from the timing system 10 wherein f=50 K Hz, 2f=100 K Hz and 4f=200 K Hz. These frequencies are typical examples and should not be considered as limiting invention as any convenient frequency and its multiples could be used to operate the line decoder. The operation of the digital filter 98 is based upon the use of the convolution integral. First consider the RC network, eight-pole switching arrangement, the internal switches of the line decoder make one complete revolution in a period T, and each has a dwell time on each contact of T/8 (this avoids shorting two adjacent capacitors together). For example, when the switches are all open except the eighth position, the eighth capacitor 41 is shunted across the output and all other capacitors are floating. The selection of eight switches and capacitors is arbitrary, in that N capacitors and N switching may be utilized providing N is greater than 3. If all of the capacitors are equal, for example, then the aforementioned eighth path through the system provides the resistor 100 and capacitor 41 to ground.

It should be apparent that the line decoder element AM3705CD includes a connection to the negative system ground potential. The principle of operation of the digital filter is that the average frequency at the input to the filter is equal to 50 K Hz, as seen from the central timing system 10, each time the internal switches sequence from the three-line to eight-line decoder is repeated, capacitors 41, see the same voltage and eventually charge up to a pre-determined level. As the frequency of the input Vo differs from the frequency supplied from the timing system 10 to the filter frequency input, each of the capacitors see a slightly different voltage and presents a change of impedance to ground on resistor 100, thereby changing the output level to the AC/DC converter 19. Once the input frequency to filter 98 falls considerably outside of the filters 7 Hz bandpass, the characteristics of this filter are identical to a conventional LC type bandpass filter having a Q of around 7000.

The output from the unity gain amplifier 102 supplies an input to AC/DC converter 19. The converter 19 includes a series capacitor 122 of 0.01 µf and a series diode 124 connected to the input of summing junction 126. At the summing junction, between capacitor 122 and diode 124, is a second diode 128 with its anode connected to the system ground potential. Both diodes are of the type 1N4454 connected at the junction between diode 124 and the summing junction 126 is a capacitor 129 of 0.1 µf which is also tied to system ground potential. The AC/DC converter 19 generates a DC equivalent of the high Q filter input voltage Vo which is applied through resistor 130 of 100 K ohms to the summing junction 126. The AC/DC converter chosen for 19 is only one of many types of AC/DC converters available. That is, a design such as shown for AC/DC converter 21 could also be used for AC/DC converter 19.

The summing junction includes parallel resistor 132, which is connected to −Vref, and a capacitor 134 which is connected to the system negative potential. Resistor 132 is 100K ohms ±1% of MF construction and capacitor 134 of 0.1 µf. In the summing junction, the voltage at the output of the AC/DC converter 19 is compared with the voltage generated by the negative reference voltage −Vref.

The output signal Verr from the summing junction 126 is connected to the positive input of operational amplifier 135 of the type 2M224. The negative input of the operational amplifier 135 is connected to the system ground potential through resistor 138 of approximately 470 ohms. The negative input of this operational amplifier is tied to its output through two parallel paths. One path is through a resistor 140 of 200 K ohms, the other path is through a transistor 142 MOS FET switch of the type M511, whose drain is tied to the negative input of 135 and the source element is in series with a resistor 145 of 22 K ohms. The gate element of transistor switch 142 is tied to the system positive or negative potential ±V through external switch 144.

The output of the digital bandpass filter 98 is applied through a simple AC/DC converter which generates a DC equivalent of the peak to peak voltage Vo which is then applied through resistor 130 to the summing junction 126. At the summing junction, the voltage at the output of the AC/DC converter is compared with the negative voltage $-V_{ref}$ from source 39. When resistors 130 and 132 are substantially equal in value, the output of the AC/DC converter will have an error voltage Verr which is directly proportional to the difference between Vo and $-V_{ref}$. The Verr error signal is then applied through a high-gain DC amplifier which is mechanized through utilization of the operational amplifier 135, resistors 138, 140 when switch 144 is in its open position. When switch 144 is in its closed position, transistor 142 closes the circuit through resistor 145 to form a parallel load path across resistor 140, this reduces the gain of the amplifier 135 by precisely a factor of 10. The output $V_1$ from operational amplifier 135 is connected to several parallel paths. One of these paths is to a base line restorer 146. The base line restorer circuit provides the elimination of any DC offset which may exist in the signal $V_1$. The input to the base line restorer is fed through a variable resistor 148 having a range of from substantially zero ohms to 10K ohms. The wiper arm 149 of resistor 148 is connected to two parallel paths. One path provides a positive input to an operational amplifier 150 through a series resistor 152 of approximately 470 K ohms. The positive input to the operational amplifier 150 is also connected through capacitor 154 of 2 $\mu f$. The negative input to operational amplifier 150 is connected to its output through resistor 156 of 470 K ohms. The output of operational amplifier 150 is connected through resistor 158 of 100 K ohms to the positive input of operational amplifier 160. The positive input to operational amplifier 160 is tied to the negative ground potential through parallel connected capacitor 162 of 0.027 $\mu f$ and resistor 164 of 390 K ohms. The other parallel path from the wiper 149 of resistor 148 is connected through resistor 166 of 100 K ohms to the negative input of operational amplifier 160. The negative input of operational amplifier 160 is further connected to its output through two parallel paths. One path through resistor 168 of 390 K ohms and the other through capacitor 170 of 0.27 $\mu f$. Resistor 152 and capacitor 154 provide for the lower band edge of the bandpass filtering characteristic of the base line restorer. Resistor 152 and capacitor 154 are selected to allow the $-3$ db point to occur at 0.2 Hz. The operational amplifier 160 utilizes capacitor 170 and resistor 166 in conjunction with resistor 168 to provide for the upper band edge of this bandpass requirement of approximately 7 Hz. The mechanization of the baseline restorer is well known in the industry and is therefore neither described nor explained in more specific detail. The output voltage signal of the baseline restorer is a voltage level exactly proportional to the percentage change in the resistance of the biological sample due to blood flow represented as $\Delta R_n/R_n$.

As hereinbefore referenced, the gate element of transistor 88 (see FIG. 4) is connected to the output of a detector loop filter comprising a lead-lag filter 172, a loop integrator 174, and an acquisition aid 176. The input to loop integrator 174 is provided from $V_1$, the output signal from operational amplifier 135. This input $V_1$ is connected through resistor 178 of 2 megohms to the negative input to an operational amplifier 180. The positive input to operational amplifier 180 is connected to the system ground potential through a resistor 182 of 2 megohms. Resistor 178 like resistor 140 is provided with a shunt resistor 184 of 220 K ohms in series with the drain and source elements of a transistor switch 186 of the MOS FET channel type M511. The gate element of this switch 186 is connected through switch 188 to either the positive or negative operational potential. For practical purposes this switch 188 is ganged together with switch 144 for simultaneous operation so that both the high gain amplifier 135 and the loop integrator 174 are both set to the same gain conditions.

The input of operational amplifier 180 is connected to its negative input through capacitor 190 of 20 $\mu f$. The output signal $V_2$ from operational amplifier 180 follows two paths. One path provides an input to the lead-lag filter 172 and the other provides an input to acquistion aid 176. The input from $V_2$ to the lead-lag filter 172 provides an input to the positive input of an operational amplifier 192 through series resistors 194, 196 of 200 K ohms and 1 megohm respectfully. The positive input to operational amplifier 192 is additionally connected to the negative operational potential through capacitor 198 of 10 $\mu f$. The negative input to operational amplifier 192 is connected to its output through a resistor 200 of 1 megohm. The output of the operational amplifier 192 is connected through resistor 201 of 20 K ohms to the junction between resistor 194 and 196 provides the fine AGC input $V_3$ to the gate of the transistor 88. The input to acquisition aid 176 provides an input to two parallel back to back diodes 202 of the low leakage type FD300. The outputs of these diodes are connected to the positive input of operational amplifier 192 through resistor 204 of 10 K ohms. The loop integrator 174 is mechanized through utilization of operational amplifier 180, with capacitor 190 and resistor 178 forming the integration time constant in the high sensitivity (open) position of switch 188. When in the low sensitivity position, transistor switch 186 causes resistor 184 to appear in parallel with resistor 178. This condition reduces the loop integration time constant in the low sensitivity position by precisely a factor of 10, thereby preserving the total overall loop bandwidth of this detector as a constant independent of operator selection of the high or low sensitivity mode of operation.

The output of the loop integrator 174 generates error voltage $V_2$ which is applied to the lead-lag filter 172. A lead-lag filter is required in a closed loop systems of this type to optimize both loop bandwidth and the system damping factor. The lag time consists of resistors 194 and the effective capacitance generated by the capacitance multiplier. That is, the capacitance is equal to capacitor 198 times the value of resistor 200 divided by the value of resistor 201. This mechanization is well known in the electronics art. The lead time constant consists of resistor 201 and the effective capacitance generated by the capacitance multiplier. These time constants are very long (loop bandwidths very narrow) when the effective capacitance approaches 10,000 $\mu f$, therefore, to minimize physical space requirements for the mechanization of this order to capacitance and minimize acquistion time, this capacitance multiplier is necessary. The acquisition aid 176 comprises resistor 204 and back to back diodes 202. These diodes are selected for extreme low leakage and for extremely high impedence once the voltage across capacitor 198 and voltage level of $V_2$ is different by a value of less than 0.5 volts, so as to restore the lead-lag time constants. Upon initial acquisition, either diode 202 is forward biased. Capacitor 198 is immediately charged within several seconds, to within 0.5 volts of the voltage level at $V_2$ through the charging resistor 204. This technique bypasses the operational capacitor circuit of 192 and the value of resistor 200 divided by the value of resistor 201 which, therefore, immediately generates voltages $V_3$ (fine AGC) to a value within 0.5 volts of its final value. The remainder of the time necessary for acquisition is associated with the charging time to bring the level of $V_2$ equal to the level of $V_3$ which is determined by the time constant associated with resistor 194 and the capacitance generated by the capacitance multiplier, hereinbefore mentioned. To achieve this remaining final AGC voltage, a period of time of approximately 20-30 seconds is required before usable data may be obtained from the system.

Referring again to FIG. 5, the output of each detector is fed into the central processor 18. The central processor comprises a multiplexer 206 which receives the signal (Rn) and the signal $\Delta Rn/Rn$ outputs from each detector 16. The Rn being the resistance of each biological segment and $\Delta Rn/Rn$ being the percentage change in resistance of each biological segment with respect ot the source resistance 20 of the biological segments. It should be noted that each detector 16 supplies these outputs for their given biological segment. The multiplexer receives all of the data from all of the detectors and in a predetermined time sequence supplies one detector's output to the input of analog to digital converter 208. A parallel path from the input to the multiplexer 206 may be supplied to any convenient multichannel oscillograph 210.

The analog to digital converter 208 digitizes all of the parameters and, when applied through the output organizor 212 provides for serial PCM telemetry to communications systems (not shown) and parallel digital data for interfacing with digital computers, (not shown), via the code converter 214. In addition, the output of this code converter 214 is applied to a front panel, quick-look, single-word display 215 to allow the operator to observe data from any detector. The detector output (channel) to be observed is selected by the channel number select 216 by the operator. The output of code converter 214 is also applied through a time division distributor and digital storage registers 218 to allow for storage of the digitized source resistance Rn for each of the detectors 16. This digitized representation of the source resistance Rn provides the forward looking AGC (course AGC) which must be fed to each of the associated detectors 16 to aid in the voltage normalization processes hereinbefore discussed. The digitized output from each detector is connected to as associated input of the digital resistance converter.

A time delay of a significant number of seconds (approximately 20 to 30) is required in order to allow each of the detectors within a given system to settle to their final operational values. This is because of the low information rates of blood flow data, the "operational readiness" status from each detector is provided through comparators 219 to a detector status display 220.

Prior to attaching the constant current source to the skin segment, the operator must calibrate all of the detectors 16 and the processing equipment. The output of the precision limiter (a precise ±0.1% amplitude modulation during calibration cycle) is applied to the $V_N$ input of each detector with a resistance of known value between the electrodes in place of the skin resistance Rn. The gains of each detector is set equal by the adjustment of wiper 149 of variable resistor 148 and the processing equipment gains are set so that each channel output is equal.

Although specific manufacturer's component identification numbers have been set out in the description or any equivalent thereof may be substituted to practice the invention.

It wll be understood that changes and modifications may be made to the circuitry described above without departing from the spirit and scope of the invention as set forth in the claims appended hereto.

Having thus described the invention, what is claimed as new and useful and desired to be secured by United States Letters Patent is:

1. In a multi-channel vascular flow monitoring system comprising:
    means for applying a constant current through a skin segment for providing an AC voltage thereacross;
    means for monitoring increments of said AC voltage across a plurality of separate skin areas within said skin segment and producing a first voltage signal representative of the resistance across each of said plurality of separate skin areas and a second voltage signal representative of the percentage change of said resistance of each of said plurality of separate skin areas responsive to the vascular flow adjacent thereto;
    means for directly measuring each of said first and second voltage signal and separate means for normalizing all of said second voltage signals; and
    said monitoring means including detector means comprising a dynamic wide range AC amplifier with a narrow band, high Q, filter and an AC to DC converter having an input from the output of the filter; and said means for normalizing including a loop integrator filter.

2. The invention as defined in claim 1, additionally comprising a central processor means for receiving and processing said first and second voltage signals into a selected, useful form and providing an input voltage signal to said separate means for normalizing.

3. The invention as defined in claim 2, wherein said selected form is analog.

4. The invention as defined in claim 2, wherein said selected form is digital.

5. The invention as defined in claim 1, wherein said means for monitoring said increments of said AC voltage comprise a plurality of voltage electrodes and detector means connected thereto equal in number to said plurality of separate skin areas, said means for normalizing further includes an acquisition aid for minimizing voltage normalization time.

6. The invention as defined in claim 5, wherein each of said detector means comprises a high gain AC amplifier having an input from the output of one of said plurality of voltage electrodes, a high Q narrow bandpass filter having an input from the output of said high gain AC amplifier, a first AC to DC converter having an input from the output of said high Q narrow bandpass filter, a summing junction having an input from the output of said AC to DC converter, a source of reference voltage connected to said summing junction, a high gain DC amplifier having an input from said summing junction, the output of said high gain DC amplifier providing said second voltage signal, a second AC to DC converter having an input from said one of said plurality of voltage electrodes, the output of said second AC to DC converter providing said first voltage signal.

7. The invention as defined in claim 6, wherein said means for normalizing comprises means for connecting said second voltage signal to said high gain AC amplifier as a first feedback voltage signal to establish its gain and means for providing a second feedback voltage signal to said high gain AC amplifier for varying its gain set by said first feedback voltage signal.

8. An improved multiple channel vascular flow monitoring system comprising:
- a constant AC current source supplied by an AC voltage of a pre-selected output frequency;
- a pair of current electrodes connected to said constant current source for providing current flow through a biological segment when in direct contact therewith;
- a plurality of pairs of voltage electrodes each pair for monitoring increments of said AC voltage across separate areas of said biological segment, said increments of said AC voltage being representative of the resistance of said separate areas;
- a plurality of detector means one connected to each pair of said voltage electrodes, each detector means comprising series connected first amplifying means, a first filtering means and a first AC to DC converter means, said detector means amplifying, filtering and converting said increments of said AC voltage to a first equivalent DC voltage, a second amplifying means for amplifying said DC voltage, this amplified DC voltage being representative of the percentage change of said resistance of said separate area;
- a plurality of second AC to DC converter means for converting said increments of said AC voltage from said each pair of electrodes from AC voltage to a second equivalent DC voltage;
- means for providing a fixed gain level to said first amplifying means of each detector means responsive to said second equivalent DC voltage;
- means for providing a control on said means for providing a fixed gain level for varying said fixed gain level of said first amplifying means of each detector means responsive to the DC component of the percentage of change of said resistance of their respective separate areas;
- a plurality of base line restorer means each having its input connected to the output of its respective second amplifying means of eliminating DC offsets in the DC voltage representative of the percentage change of said resistance of said separate areas; and
- means for selectively displaying at least the outputs of one detector means.

9. The invention as defined in claim 8, wherein one of a plurality of high input impedance buffers having an impedance greater than 2 megohms at said preset output frequency is connected in series between each pair of said voltage electrodes and said first amplifying means and said second AC to DC converter means.

10. The invention as defined in claim 8, wherein said filtering means comprises an electronic switching means having at least three separately activated switch elements sequentially operated, only one of said switch elements being closed at a time, one end of each of said switch elements being connected to the system ground, the other end of lach of said switch elements being connected to a common line through a capacitor, all of the capacitors having an equal electrical value, said common line is connected at one end to the input of said first AC to DC converter means and the other end is connected through a resistor element to the output of said first amplifying means.

11. The invention as defined in claim 8, wherein said means for providing said fixed gain level to each of said first amplifying means comprises:
- means for converting said second equivalent DC voltage to a digital signal;
- memory means for storing said digital signal;
- switching means having a plurality of normally open switch elements utilizing the stored digital signal for closing selected switch elements;
- a source of system voltage;
- a plurality of resistor elements, one of said resistor elements connected in parallel with one of said switch elements, all of said plurality of resistor elements being connected in series, the resistor elements parallel with said switch elements closed by said digital signal being shorted and the total resistance of those resistors in parallel with unactuated switch elements controlling the level of gain of said first amplifying means.

* * * * *